(12) United States Patent
Grant et al.

(10) Patent No.: US 9,327,001 B2
(45) Date of Patent: May 3, 2016

(54) NUTRITIONAL SUPPLEMENT FOR WEIGHT MANAGEMENT

(71) Applicant: University of Florida Research Foundation, Inc., Gainesville, FL (US)

(72) Inventors: Maria Grant, Archer, FL (US); Ashay D. Bhatwadekar, Gainesville, FL (US); Debra Carnegie, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/356,197

(22) PCT Filed: Nov. 5, 2012

(86) PCT No.: PCT/US2012/063532
§ 371 (c)(1),
(2) Date: May 5, 2014

(87) PCT Pub. No.: WO2013/067485
PCT Pub. Date: May 10, 2013

(65) Prior Publication Data
US 2014/0286923 A1   Sep. 25, 2014

Related U.S. Application Data

(60) Provisional application No. 61/555,027, filed on Nov. 3, 2011.

(51) Int. Cl.
| | |
|---|---|
| A61K 38/43 | (2006.01) |
| A61K 36/24 | (2006.01) |
| A61K 45/06 | (2006.01) |
| A61K 36/27 | (2006.01) |
| A23L 1/30 | (2006.01) |
| A61K 31/122 | (2006.01) |
| A61K 31/19 | (2006.01) |
| A61K 31/197 | (2006.01) |
| A61K 31/355 | (2006.01) |
| A61K 31/375 | (2006.01) |
| A61K 31/385 | (2006.01) |
| A61K 33/08 | (2006.01) |
| A61K 33/24 | (2006.01) |
| A61K 36/54 | (2006.01) |
| A61K 38/05 | (2006.01) |
| A23L 1/304 | (2006.01) |

(52) U.S. Cl.
CPC ............... *A61K 36/24* (2013.01); *A23L 1/3002* (2013.01); *A23L 1/304* (2013.01); *A61K 31/122* (2013.01); *A61K 31/19* (2013.01); *A61K 31/197* (2013.01); *A61K 31/355* (2013.01); *A61K 31/375* (2013.01); *A61K 31/385* (2013.01); *A61K 33/08* (2013.01); *A61K 33/24* (2013.01); *A61K 36/27* (2013.01); *A61K 36/54* (2013.01); *A61K 38/05* (2013.01); *A61K 45/06* (2013.01); *A23V 2002/00* (2013.01)

(58) Field of Classification Search
CPC ....................................................... A61K 45/06
See application file for complete search history.

(56) References Cited

U.S. PATENT DOCUMENTS

| | | | |
|---|---|---|---|
| 5,087,472 A | 2/1992 | Nissen | |
| 5,360,613 A | 11/1994 | Nissen | |
| 5,976,550 A | 11/1999 | Engel et al. | |
| 6,031,000 A | 2/2000 | Nissen et al. | |
| 6,103,764 A | 8/2000 | Nissen | |
| 7,855,181 B2 * | 12/2010 | Neu | 514/21.91 |
| 2002/0192308 A1 | 12/2002 | Mamana | |
| 2005/0027005 A1 | 2/2005 | Boldt | |
| 2008/0305096 A1 * | 12/2008 | Verdegem et al. | 424/94.4 |
| 2009/0142443 A1 * | 6/2009 | Robinson et al. | 426/5 |
| 2010/0179112 A1 | 7/2010 | Rathmacher et al. | |
| 2011/0305799 A1 | 12/2011 | DeWille et al. | |

FOREIGN PATENT DOCUMENTS

| | | |
|---|---|---|
| WO | 2006045112 A2 | 4/2006 |
| WO | 2006079056 A1 | 7/2006 |
| WO | 2010054469 A1 | 5/2010 |

* cited by examiner

*Primary Examiner* — Bin Shen

(74) *Attorney, Agent, or Firm* — Timothy H. Van Dyke; Beusse, Wolter, Sanks & Maire, PLLC

(57) ABSTRACT

According to one embodiment, a nutritional supplement for suppressing an appetite while maintaining muscle mass of a subject during weight loss is provided. The nutritional supplement includes beta-hydroxy beta-methylbutyric acid (HMB), chromium, and *Caralluma fimbriata*.

10 Claims, No Drawings

NUTRITIONAL SUPPLEMENT FOR WEIGHT MANAGEMENT

CROSS-REFERENCE TO RELATED APPLICATIONS

This application is related to U.S. Provisional Application No. 61/555,027 filed Nov. 3, 2011, priority to which is claimed under 35 USC 119.

INTRODUCTION

Obesity has been recognized as a public health problem in the United States and throughout the world. Overweight or obese individuals are at a higher risk for developing diseases such as hypertension, dyslipidemia, type-2 diabetes (non-insulin dependent diabetes mellitus or NIDDM), coronary heart disease, stroke, gallbladder diseases, osteoarthritis, sleep apnea, and respiratory problems. Obesity is also associated with a higher prevalence of endometrial, breast, prostate and colon cancers. It is therefore not surprising that obesity is also associated with increased mortality and premature death. The pharmaceutical industry has developed drugs to help people lose weight. However, no drug has been discovered that allows individuals to eat all they desire and retain a sedentary lifestyle while simultaneously losing weight. Furthermore, the drug products available to the general public, whether by prescription or as over-the-counter preparations, are not free of risk. Known risks include valvular heart disease arising out of the use of the combination of fenfluramine and phentermine (Fen-Phen), and irregular heart beat (arrhythmia) that is associated with the use of phenylpropanolamine (PPA). These risks have resulted in bans on the use of these drugs in weight loss products and programs in some countries. Health risks of anti-obesity preparations are not limited to prescription and/or over-the-counter medications. The use of ephedra in nutritional products employed for weight loss has been associated with arrhythmia and even sudden death in susceptible individuals. A great concern regarding weight loss and the use of nutritional supplements and compositions, therefore, is a health risk concern. Another concern in weight loss is the breakdown of muscles.

Prevention or inhibition of muscle breakdown and the facilitation of efficient muscle repair is of great interest to athletes, the elderly, and those with muscle-wasting conditions. A wide range of products and methods have been proposed for enhancing healthy muscle tissues and enhancing athletic performance. Existing compositions and methods which are available for these purposes suffer from a variety of shortcomings. These shortcomings range from potentially dangerous side effects to a lack of bioavailability and difficulty in formulation or administration.

It is well known that proteins are converted to amino acids in the digestive system and that the resulting amino acids are used by the body for growth and development. In certain medical situations a patient may be unable to receive proteins. In these situations patients have been given free amino acids. Free amino acids, however, are sometimes not tolerated well by patients and may cause diarrhea and dehydration. Also, the free amino acids may be unstable and/or difficult to formulate. It has been observed that the body can more effectively absorb certain small molecules called dipeptides or tripeptides. These molecules consist of, for example, two to three amino acids. It has been observed, for example, that peptides containing the amino acid residue glycine in the N-terminal position are readily assimilable. See for example, U.S. Pat. No. 4,340,592.

Regulation of the intake of calories as well as body composition during the weight loss process can provide positive results. However, food cravings are very common and a weight loss program or diet including a reduced caloric intake usually induces cravings for food that reduce adherence to weight loss regimens. These cravings are caused by both psychological and physiological mechanisms. For example, ingested carbohydrates are absorbed from the digestive tract into the bloodstream to increase blood glucose levels. In response to the increase in blood glucose, the pancreas releases insulin to aid in the transport of glucose into the cells of the body where glucose is employed as an energy source. However, if the amount of insulin released is greater than the amount of glucose present (which is often the case in overweight individuals), then the body reacts by signaling the brain to ingest more carbohydrates in order to balance the amount of insulin in the bloodstream. This insulin-induced craving for carbohydrates is very common during periods of caloric restriction. In spite of extensive prior research, there is still a need for a weight-loss product that helps promote a sensation of satiety to assist with a reduction in caloric intake, while substantially preserving lean body mass as weight loss occurs. Although many researchers have contributed to the complex body of knowledge about physiologic energy utilization under conditions of caloric restriction, existing nutritional supplements and regimens still result in an undesired loss of lean body mass.

SUMMARY

The subject invention is based on the inventors surprising discovery that administration of a composition or nutritional supplement containing a particular combination of metabolites, vitamins, plant extracts, anti-oxidants, chemicals, minerals, and natural compounds reduces insulin sensitivity, maintains lean muscle mass during weight loss, and provides a key appetite suppressant in animals. The composition is administered between meals, in one embodiment, as a snack alternative to suppress hunger and minimize overeating at meal time.

DETAILED DESCRIPTION

Explanation of Terms

"Administering" or "administration" as used herein includes self-administration by the subject, administration by another to the subject, and providing advice for administration to the subject (as in instructions provided in a tangible medium, such as printed instructions or advice on a computer readable medium). Administration by another to the subject can include, for example, administration by a physician, nurse or other health care provider or dietary consultant. Administration also includes providing an end product (such as a mixed beverage) that is consumed, or precursors that contain the end product (such as a powdered mix to be dispensed in a beverage) that another (such as the subject) may prepare for consumption.

Administration includes but is not limited to oral or intravenous administration by liquid, capsule, tablet, or spray. Administration may be by injection, whether intramuscular, intravenous, intraperitoneal or by any parenteral route. Parenteral administration can be by bolus injection or by continuous infusion. Formulations for injection may be presented in unit dosage form, for example, in ampoules or in multi-dose containers with an added preservative. The compositions may take the form of suspensions, solutions or emulsions in oily or aqueous vehicles and may contain formulatory agents such as suspending, stabilizing and/or dispersing agents. Alternatively the compositions may be in powder form (e.g., lyophilized) for constitution with a suitable vehicle, for example sterile pyrogen-free water, before use. Compositions may be delivered to a subject by inhalation by any presently known suitable technique including a pressurized aerosol spray, where the dosage unit may be controlled using a valve to deliver a metered amount.

Administration by capsule and cartridges containing powder mix of the composition can be used in an inhaler or insufflator to deliver the particles to the subject.

Amounts expressed herein as percentages are percentages by weight unless indicated otherwise.

As used herein, the terms "individual" or "subject" refer to an animal, such as a mammal, for example a human.

A "shake mix" or "drink mix" or "beverage mix" or "powder" refers to a mixture, such as a powdered mixture, that is suitable for mixing in a liquid base (such as water or milk) to provide a beverage in which the mixture is dispensed to a subject. The shake mixture increases the thickness of the liquid base.

According to one embodiment, a nutritional supplement for suppressing an appetite while maintaining muscle mass of a subject during weight loss is provided. According to this embodiment, the nutritional supplement includes beta-hydroxy beta-methylbutyric acid (HMB), chromium, and *Caralluma fimbriata*. These components work together in an additive, or synergistic way, to suppress appetite which maintaining muscle mass. HMB is a metabolite of leucine, and promotes lean muscle mass. The branched chain amino acids (BCAAs) leucine, isoleucine, and valine make up more than one third of muscle protein. Harper A E, Miller R H, Block K P: Branched-chain amino acid metabolism. *Annu Rev Nutr* 1984, 4:409-454.

Of these, the most investigated BCAA is leucine see Hider R C, Fern E B, London D R: Relationship between intracellular amino acids and protein synthesis in the extensor digitorum longus muscle of rats. *Biochem J* 1960, 114(2):171-178. Under normal bodily conditions, approximately 5% of leucine is metabolized into HMB. Van Kovering M, Nissen S L: Oxidation of leucine and alpha-ketoisocaproate to b-hydroxy-b-methlbutyrate in vivo. *Am J Physiol Endocrinol Metab* 1992, 262:27. *Caralluma fimbriata* is a medicinal plant from the family Asclepiadacea. *Caralluma* provides a suppressant of hunger and appetite and enhances stamina. It is a genus of edible cacti, and grows across India. See: www.fda.gov/ohrms/dockets/dockets/95s0316/95s-0316-rpt0252-08-exhibit-02-vol184.pdf.

According to a further embodiment, the nutritional supplement formulation described above further includes magnesium oxide, alpha lipoic acid, Coenzyme Q10 (CoQ10), vitamin C, vitamin E, and/or cinnamon. Without being bound to any particular theory, it is believed that these compounds work together, synergistically, to reduce insulin sensitivity by optimizing mitochondrial ATP generation with the use of critical co-factors and anti-oxidant combinations. Additionally, the nutritional supplement provides benefits including the aforementioned appetite suppressant as well as the improvement of pancreatic function. In particular embodiments, the nutritional supplement includes at least 1200 mg HMB, at least 100 mcg chromium, at least 400 mg *Caralluma fimbriata*, at least 30 mg magnesium oxide, at least 50 mg alpha lipoic acid, and at least 15 mg of CoQ10.

According to a specific embodiment, a composition including an appetite suppressing and lean muscle mass augmentation and/or preservation amount of a synergistic composition is provided, the composition includes: *Caralluma fimbriata*, HMB, chromium, magnesium oxide, cinnamon, vitamin C, vitamin E, alpha lipoic acid, and CoQ10.

The terms "synergy" or "synergistic" or "synergistically" as used herein refers to an effect achieved when individual components are combined, wherein the total effect achieved by their combination is greater than the effect of the sum of the two or more components. In particular embodiments, synergy as used herein means that appetite suppression, reduction of insulin sensitivity, or lean muscle preservation is greater than that obtained by increasing the dose of either constituent administered alone. Thus, for example, the effect of adding components together to produce a first supplement of a certain amount is greater than the effect achieved by producing a second supplement of the same amount with only one component or fewer components than that in the first supplement.

The synergistic composition provided by the subject invention combining *Caralluma fimbriata*, HMB, chromium, magnesium oxide, cinnamon, vitamin C, vitamin E, alpha lipoic acid, and CoQ10 results in a never heretofore discovered synergistic effect. This synergistic effect results in simultaneously suppressing appetite and achieving lean muscle mass augmentation and/or preservation in a way that has never been accomplished before, and never been accomplished, particularly, with the use of only one composition or nutritional supplement.

According to another embodiment, the invention pertains to a method of providing a synergistic appetite suppressing activity to a subject. The method includes administering to the subject a food item comprising HMB, chromium, *Caralluma fimbriata*, magnesium oxide, alpha lipoic acid, CoQ10, cinnamon, vitamin E, and vitamin C.

In a further embodiment, the method is provided wherein the food item includes an admixture of at least 1200 mg of HMB, at least 100 mcg chromium, at least 400 mg of *Caralluma fimbriata*, at least 300 mg of magnesium oxide, at least 50 mg of alpha lipoic acid, at least 15 mg of CoQ10, at least 300 mg cinnamon, and 300 IU each of vitamins E and C disposed in a capsule or within a tablet. In a specific embodiment, the capsule or tablet includes 250 mg of the admixture. However the capsule or tablet may be, but is not limited to, from 10 to 500 mg total weight. In other specific embodiments, the capsules are 25, 50, 75, 100, 125, 150, 175, 200, 225, 250, 275, 300, 325, 350, 375, 400, 425, 450, 475, or 500 mg, total individual weight.

In another embodiment, a nutritional supplement for suppressing an appetite while maintaining muscle mass of a subject during weight loss is provided. This nutritional supplement includes between 1200-1800 mg HMB, 100-200 mcg chromium, 400-600 mg *Caralluma fimbriata*, 30-70 mg magnesium oxide, 50-150 mg alpha lipoic acid, 15-45 mg Coenzyme Q10 (CoQ10), 300-500 IU vitamin C, 300-500 IU vitamin E, 300-700 mg cinnamon; and a flavoring. The amount of flavoring may vary based on the weight and size of the nutritional supplement. The nutritional supplement may be provided in various forms including but not limited to a nutritional bar, a shake, a powder form, tablet, capsule, gum, candy, and/or an orally or parenterally administrable liquid.

The embodiments described herein may also include an effective amount of a peptide to inhibit breakdown of muscle loss. Examples of such peptides include a dipeptide and other peptides described in U.S. Pat. Nos. 8,133,868 and 7,855,181. In specific examples the dipeptide pertains to an arginyl-glutamine dipeptide, wherein the arginine residue is the amino terminus of said dipeptide and the glutamine residue is the carboxy terminus of said dipeptide.

According to another embodiment, a food item is provided, the food item for suppressing appetite while maintaining muscle mass in a subject. The food item including a 40 gram food item which includes at least 3% by weight HMB, at least 0.00025% by weight chromium, at least 1% by weight *Caralluma fimbriata*, at least 0.075% by weight magnesium oxide, at least 0.125% by weight alpha lipoic acid, at least 0.375% by weight Coenzyme Q10 (CoQ10), at least 0.5% by weight vitamin C, at least 0.5% by weight vitamin E, at least 0.75% by weight cinnamon, between 1% and 94% by weight flavoring, and a peptide composition comprising an arginyl-glutamine dipeptide formulated as a nutrient formulation, wherein the arginine residue is the amino terminus of said dipeptide and the glutamine residue is the carboxy terminus of said dipeptide. In a further embodiment, the food item is provided in which it includes a nutritional bar, shake, powder, tablet, capsule, gum, candy, and/or an orally or parenterally administrable liquid.

According to another embodiment, a food item is provided which includes an amount effective to reduce or suppress appetite in a subject while maintaining muscle mass in the subject. The food item may be provided as detailed in the chart below, including example sources for each ingredient listed. Each food item may contain, in one embodiment, the following:

| INGREDIENT | QUANTITY | SOURCE |
|---|---|---|
| *Caralluma fimbriata* powder | 500 mg | Federal Laboratories Chemical Corporation, Alden, New York |
| Chormium Picolinate Plus | 200 µg (One tablet each) | CVS Pharmacy Inc, Woonsocket, RI |
| Magnesium Citrate | 50 mg | Now Foods, Bloomingdale, IL |
| Cinnamon Powder | 500 mg | McCormic & Co Inc, Hunt Valley, MD, |
| Vitamin C crystals | 500 mg | Wholesale Nutrition, Palatine, IL |
| Vitamin E powder | 400 IU | Wholesale Nutrition, Palatine, IL |
| Alpha-lipoic acid | 100 mg | Superior Nutraceuticals Inc, Marietta Ga |
| Coenzyme Q-10 | 30 mg | Wholesale Nutrition, Palatine, IL |
| Creatine Monohydrate | 3 gm | Optimum Nutrition, Aurora, IL |

*Caralluma* powder is commercially available, and can be obtained from *caralluma fimbriata* chips. *Caralluma* powder conforms to California's Proposition 65 which regulates toxic substances according to the Federal Laboratories Corp. Details of a sample of *caralluma* powder include a green to brownish powder appearance, between 68-80 mesh particle size, characteristic taste and odor, <7% moisture (one specific example includes 4.5%), <11% ash (one specific example includes 8.3%), 5-7 pH (one specific example include 5.2 pH), <0.01 ppm lead, mercury, cadmium, and arsenic, 0.350-0.450 g/cc bulk density (one particular example contains 0.386 g/cc), and 0.550-0.750 g/cc tap density (one particular example contains 0.560 g/cc). Further details include <1000 CFU/G, negative results for *salmonella, e.coli, staphylococcus aureus*, and <100 CFR/G yeast/molds. The specific example described includes *caralluma* powder derived from *caralluma fimbriata* chips, manufactured in Buffalo, N.Y., (sample ID# C-082806).

In certain embodiments, the compositions, nutritional supplements, and food items described herein will generally be used in an amount effective to achieve the intended purpose. For use to treat or prevent the abovementioned diseases or disorders or for use in suppressing appetite, increasing protein synthesis and inhibiting muscle proteolysis, reducing insulin sensitivity, and maintaining muscle mass during weight and fat loss, the compositions, supplements and food items will be administered or applied in a therapeutically effective amount.

Dosage may be delivered in a single administration by multiple applications or controlled release. In one embodiment, the compositions of the invention are delivered by oral sustained release administration. Preferably, in this embodiment, the compositions are administered twice per day (more preferably, once per day). Dosing may be repeated intermittently, may be provided alone or in combination with other compositions and or supplements and/or food items and may continue as long as required for effective treatment of the disease state or disorder, or to achieve one of the benefits mentioned above.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described.

Those skilled in the art of medicinal chemistry and pharmaceutical formulations will appreciate that other formulations can be devised for appropriate oral, parenteral or other administration. U.S. Pat. Nos. 6,821,532 and 7,157,493 are cited for general background of pharmaceutical formulations.

While the principles of the invention have been made clear in illustrative embodiments, there will be immediately apparent to those skilled in the art, in view of the teachings herein, many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

The references referred to herein are incorporated herein in their entirety to the extent they are not inconsistent with the teachings herein.

We claim:

1. A nutritional supplement for suppressing an appetite while maintaining muscle mass of a subject during weight loss, comprising:
   beta-hydroxy beta-methylbutyric acid (HMB);
   chromium; and
   *Caralluma fimbriata*, wherein said nutritional supplement is a food item comprising a nutritional bar or shake; wherein the nutritional bar or shake comprises 1200-1800 mg of HMB, 100-200 mcg of chromium, and 400-600 mg of *Caralluma fimbriata*.

2. The nutritional supplement of claim 1 further comprising:
   magnesium oxide;
   alpha lipoic acid and Coenzyme Q10 (CoQ10);
   vitamin C, vitamin E, and cinnamon.

3. The nutritional supplement of claim 2 comprising at least 30 mg of magnesium oxide in the nutritional bar or shake.

4. The nutritional supplement of claim 2 comprising at least 50 mg of alpha lipoic acid in the nutritional bar or shake.

5. The nutritional supplement of claim 2, comprising at least 15 mg of CoQ10.

6. The supplement of claim 1, further comprising a peptide composition comprising an arginyl-glutamine dipeptide, wherein the peptide is provided in an effective amount to reduce muscle breakdown or loss.

7. The supplement of claim 1, further comprising a peptide composition comprising an arginyl-glutamine dipeptide, wherein the peptide is provided in an effective amount to reduce muscle breakdown or loss.

8. A nutritional supplement for suppressing an appetite while maintaining muscle mass of a subject during weight loss, comprising:
   1200-1800 mg beta-hydroxy beta-methylbutyric acid (HMB);
   100-200 mcg chromium;
   400-600 mg *Caralluma fimbriata;*
   30-70 mg magnesium oxide;
   50-150 mg alpha lipoic acid;
   15-45 mg Coenzyme Q10 (CoQ10);
   300-500 IU vitamin C;
   300-500 IU vitamin E;
   300-700 mg cinnamon; and
   a flavoring;
   wherein the nutritional supplement is a food item comprising a nutritional bar or shake.

9. The supplement of claim 8, further comprising a peptide composition comprising an arginyl-glutamine dipeptide, wherein the peptide is provided in an effective amount to reduce muscle breakdown or loss.

10. A food item for suppressing appetite while maintaining muscle mass in a subject, comprising:
    a 40 gram food item, comprising:
        at least 3% by weight beta-hydroxy beta-methylbutyric acid (HMB);
        at least 0.00025% by weight chromium;
        at least 1% by weight *Caralluma fimbriata;*
        at least 0.075% by weight magnesium oxide;
        at least 0.125% by weight alpha lipoic acid;
        at least 0.375% by weight Coenzyme Q10 (CoQ10);
        at least 0.5% by weight vitamin C;
        at least 0.5% by weight vitamin E;
        at least 0.75% by weight cinnamon;
        between 1% and 94% by weight flavoring; and
        a peptide composition comprising an arginyl-glutamine dipeptide formulated as a nutrient formulation, wherein the arginine residue is the amino terminus of said dipeptide and the glutamine residue is the carboxy terminus of said dipeptide;
    wherein the food item comprises a nutritional bar or shake.

* * * * *